United States Patent [19]
Ribadeau-Dumas et al.

[11] Patent Number: 5,547,689
[45] Date of Patent: Aug. 20, 1996

[54] CHEWING-GUM COMPOSITION OF IMPROVED ORGANOLEPTIC QUALITY AND PROCESS ENABLING SUCH A CHEWING-GUM TO BE PREPARED

[75] Inventors: Guillaume Ribadeau-Dumas, Lambersart; Frédéric Bouvier, Lille; Michel Serpelloni, Beuvry les Bethune, all of France

[73] Assignee: Roquette Freres, Lestrem, France

[21] Appl. No.: 381,431

[22] Filed: Jan. 31, 1995

[30] Foreign Application Priority Data

Feb. 1, 1994 [FR] France ............................ 94 01082

[51] Int. Cl.⁶ ............................................. A23G 3/30
[52] U.S. Cl. ............................ 426/3; 426/5; 426/658
[58] Field of Search ...................... 426/3–6, 96, 658; 127/30

[56] References Cited

U.S. PATENT DOCUMENTS

| | | | |
|---|---|---|---|
| 3,761,286 | 9/1973 | Shepherd et al. | 426/5 |
| 3,826,847 | 7/1974 | Ogawa et al. | 426/5 |
| 3,903,305 | 9/1975 | Bahoshy et al. | 426/3 |
| 3,915,736 | 10/1975 | Oyamada et al. | 127/29 |
| 4,001,438 | 1/1977 | Marno et al. | 426/96 |
| 4,122,195 | 10/1978 | Bahoshy et al. | 426/3 |
| 4,157,401 | 6/1979 | Stroz et al. | 426/3 |
| 4,217,368 | 8/1980 | Witzel et al. | 426/5 |
| 4,408,041 | 10/1983 | Hirao et al. | 536/4.1 |
| 4,590,075 | 5/1986 | Wei et al. | 426/5 |
| 4,695,463 | 9/1987 | Yang et al. | 424/440 |
| 4,752,481 | 6/1988 | Dokuzovic | 426/3 |
| 4,803,083 | 2/1989 | Chapdelaine et al. | 426/3 |
| 4,808,418 | 2/1989 | Zamudio-Tena et al. | 426/5 |
| 4,831,129 | 5/1989 | Serpelloni | 536/124 |
| 4,849,023 | 7/1989 | Devos et al. | 124/40 |
| 4,889,727 | 12/1989 | Dave et al. | 426/3 |
| 4,900,563 | 2/1990 | Cherukuri et al. | 426/5 |
| 4,915,958 | 4/1990 | Faust et al. | 426/3 |
| 4,948,595 | 8/1990 | Patel et al. | 426/3 |
| 4,986,991 | 1/1991 | Yatka et al. | 426/3 |
| 5,004,595 | 4/1991 | Cherukuri et al. | 424/48 |
| 5,017,400 | 5/1991 | Olinger et al. | 426/660 |
| 5,075,118 | 12/1991 | Difalco, Jr. et al. | 426/3 |
| 5,110,608 | 5/1992 | Cherukuri et al. | 426/3 |
| 5,165,943 | 11/1992 | Patel et al. | 426/3 |
| 5,405,623 | 4/1995 | Barkalow et al. | 426/5 |

FOREIGN PATENT DOCUMENTS

| | | |
|---|---|---|
| 0102237 | 3/1984 | European Pat. Off. . |
| 0202885 | 11/1986 | European Pat. Off. . |
| 0265386 | 4/1988 | European Pat. Off. . |
| 0302023 | 2/1989 | European Pat. Off. . |
| 0325090 | 7/1989 | European Pat. Off. . |
| 0366251 | 5/1990 | European Pat. Off. . |
| 0401954 | 12/1990 | European Pat. Off. . |
| 0427505 | 5/1991 | European Pat. Off. . |
| 0425115 | 5/1991 | European Pat. Off. . |
| 0427541 | 5/1991 | European Pat. Off. . |
| 0453402 | 10/1991 | European Pat. Off. . |
| 0528466 | 2/1993 | European Pat. Off. . |
| 49-32067 | 8/1974 | Japan . |
| 52-27702 | 7/1977 | Japan . |
| 03133341 | 6/1991 | Japan . |
| WO84/03201 | 8/1984 | WIPO . |
| WO85/01862 | 5/1985 | WIPO . |
| WO88/08671 | 11/1988 | WIPO . |
| WO90/04926 | 5/1990 | WIPO . |
| WO90/12512 | 11/1990 | WIPO . |
| WO91/00692 | 1/1991 | WIPO . |
| WO92/05682 | 4/1992 | WIPO . |
| WO93/17577 | 9/1993 | WIPO . |

OTHER PUBLICATIONS

–"Sugar–free chewing–gum based on maltitol" by T. Maruyama et al. Shokuhin Kogyo (1984) 27, No. 24, pp. 73–80.

–"Evaluation of maltitol in eight food products . . . " R. L. De Fielliettaz Goethart et al. Basic Studies in Food Science (1983), vol. 2, pp. 8–9.

–Database WPI Week 8541, Derwent Publications Ltd., London, GB; AN 85–253398 & JP–A–60 168364 (Sekisui Chem. Ind. Co. Ltd.) Aug. 31, 1985 *abstract*.

*Primary Examiner*—Jeanette Hunter
*Attorney, Agent, or Firm*—Larson and Taylor

[57] ABSTRACT

The subject of the invention is a novel chewing-gum composition of improved organoleptic quality.

This composition contains maltitol particles of purity greater than 95%, which are distributed within the composition such that at least 50% of them are smaller than 90 microns in size.

The invention also relates to a process for the preparation of such a composition and the use of a pulverulent maltitol having very specific properties.

18 Claims, No Drawings

CHEWING-GUM COMPOSITION OF IMPROVED ORGANOLEPTIC QUALITY AND PROCESS ENABLING SUCH A CHEWING-GUM TO BE PREPARED

The present invention relates to a chewing-gum composition of improved organoleptic quality. It also relates to a process for preparing such a composition by the use of a maltitol powder which has very specific properties.

Most chewing-gums, whether they contain sugar or are sugar-free, of bubble-gum type or otherwise and sugar-coated or otherwise, essentially comprise a water-insoluble gum base, water-soluble sweetening agents provided in liquid or pulverulent form, and flavourings. They often comprise other ingredients such as dyes, emulsifiers, plasticizers, intense sweeteners, water, etc.

In a very large majority of cases, when they are formulated without sugar, the chewing-gums on the market comprise sorbitol provided in pulverulent form. The average diameter of the particles contained in the sorbitol powders used is very generally between 100 and 200 microns.

There exists in chewing-gums, and in particular in sugar-free chewing-gums, a flaw which has constantly been perceived by the consumers and which has still not been very well overcome by the formulators, although it has been and is still the subject of much research aimed at correcting it. This flaw, which is often accompanied by other flaws of an organoleptic nature, concerns the lack of impact of the flavourings in the chewing-gums and their short persistence during chewing. Thus, the retro-olfactory sensations which the flavourings present in a chewing-gum are supposed to provide are generally insufficiently intense during the first minutes of chewing and usually disappear very rapidly in the following minutes. However, the chewing-gums then considered to be tasteless quite often still contain 60 to 80% of the amount of flavouring introduced during their formulation.

Several methods have been described in the literature in order to solve the problem outlined above.

A first group of methods starts from the premise that the chewing-gum flavourings are either too poorly soluble in water, and in this case are then strongly bound to the gum base of the chewing-gum, or are too highly soluble in water, and in this case are insufficiently retained by the constituents of the chewing-gum.

In the first case, which appears to be the more common, the flavouring, on account of its poor solubility in water and in saliva, lacks impact and is perceived too weakly during the first minutes of chewing, which naturally makes its identification difficult. On the other hand, it is extracted slowly and continually by the saliva, which usually imparts to the chewing-gum a certain persistence of its flavour as a consequence.

In the second case, the flavouring, which is too poorly bound, is extracted rapidly from the chewing-gum, often even more rapidly than the water-soluble sweetening agents. In this case, the flavouring has an excellent impact in the mouth but particularly insufficient persistence.

Thus, the first group of methods aims to correct the flaws of these two types of flavourings by modifying as much as possible, and very directly, the coefficients of their distribution between, on the one hand, the gum base, and, on the other hand, the aqueous phase or the saliva, so as to impart a retro-olfactory sensation which is simultaneously strong as soon as it is placed in the mouth, and intense and continual as a consequence. In this respect, it is important to recall that in order to be considered to be of good quality by consumers, a chewing-gum should keep its flavour for 10 to 30 minutes, this time corresponding to the customary minimum and maximum chewing times.

Firstly, among this group, methods of encapsulation of the flavourings or of trapping of the latter within a matrix are known. This matrix may be hydrophilic, in which case it allows greater release of the flavouring. This is the case, for example, in the processes described in the Patents and Patent applications U.S. Pat. No. 4,122,195, WO 91/00692, U.S. Pat. No. 5,004,595, U.S. Pat. No. 4,695,463, U.S. Pat. No. 3,761,286, EP 102,237, EP 528,466 and U.S. Pat. No. 5,165,943, which respectively claim the use, in order to create these dextrin matrices, of gum arabic, of gelatin and of hydrocarbons, of hydrocolloids or of polysaccharides or of polyols, of alginates and of carrageenates, of hydroxyethyl acrylates, of zein, of microbial cells, of sorbitol and of cyclodextrins.

The encapsulating protective matrix may also be hydrophobic as recommended, for example, in the Patents and Patent applications EP 401,954, WO 84/03201, U.S. Pat. No. 3,826,847, WO 92/05682 and U.S. Pat. No. 4,590,075 which respectively describe the advantage of using rosins, lacquers or waxes, polyvinyl acetate, a mixture of styrene butadiene, starch octenyl succinate and silicone dioxide, and synthetic or natural gums.

The major drawbacks of these techniques lie in their high cost, the difficulty of putting them into practice and the risk of only incompletely recovering the combination of notes of a flavouring. This risk arises from the fact that some of these notes, in contrast with others, may in fact be masked on account of their excessive retention within the matrix, which has the detrimental consequence of then destroying the original balance of the flavouring. Secondly, among this first group of methods, more radical methods are also known, these aimed at modifying the flavouring such that it becomes more suited to the specific need of chewing-gums. In this respect, Patent EP 427,505 may be mentioned, which recommends as a solution the use of terpene-free natural essential oils. Also in this spirit, flavouring producers nowadays propose the use of flavourings specially developed for sugar-free chewing-gums, which are higher in price than those used in the standard formulations.

Methods are also known which are intermediate between the two techniques proposed above, consisting in combining an encapsulated flavouring with a suitable liquid flavouring so as to obtain both an appreciable impact and a long-lasting flavour. By way of example, reference may be made to Patents EP 265,386 and U.S. Pat. No. 4,001,438. These techniques are matters of great complexity and the drawbacks mentioned above for the encapsulated flavourings are generally encountered.

A second group of methods exploits the capacity of the gum bases to bind the flavourings. This property may optionally be adjusted so as to create a veritable pool of flavouring within the chewing-gum. This solution is recommended, for example, in Patents U.S. Pat. No. 4,915,958, U.S. Pat. No. 4,808,418 and U.S. Pat. No. 5,110,608, which claim chewing-gums having improved organoleptic properties by the use of high concentrations of gum base. This gum base must then have mechanical properties and a composition which are different from those ordinarily used, such that it is still possible to chew such chewing-gums. In order to obtain a satisfactory result, it is convenient in this case also to increase substantially the flavouring contents of the chewing-gums, which is not without consequence for their cost price.

Another solution consists in modifying the composition of the gum base. Patent application WO 93/17577 is known for example, in which it is recommended, in order to obtain the desired result, to remove the waxes ordinarily employed. It is then essential to reformulate the chewing gums entirely in order for them to have a correct binding and good plasticity.

A third group of methods consists in adding specific substances to the chewing-gums, at low concentrations, so as to correct the impact and persistence flaws of the flavourings.

It has been proposed in the Patents and Patent applications U.S. Pat. No. 4,752,481, WO 90/04926 and EP 202,885 to use emulsifiers whose hydrophilic-lipophilic balance is either less than or greater than 7, or alternatively to use soya lecithin.

Other authors have recommended the use of flavour exhausters such as salts or alternatively encapsulated salt, cocoa powder, sodium glutamate, methyl salicylate and limonene derivatives. The use of such products is, for example, justified in the Patents and Patent applications WO 90/12512, U.S. Pat. No. 4,889,727, U.S. Pat. No. 3,903,305, U.S. Pat. No. 4,948,595 and U.S. Pat. No. 4,157,401.

A number of other exhausters have been described. These are, in particular, food acids and intense sweeteners. As regards the latter, a large number of patents claim or describe the advantage of using, for example, cyclamates, aspartame, saccharin, alitame and sucralose, in free or encapsulated form, in order to improve the taste of chewing-gums, in particular of those formulated without the addition of sugar. It would appear that it is thus sought more to increase the intensity and persistence of the sweet taste than to improve the flavour sensations. Use may also be made of possible sweetening power synergies between two different intense sweeteners, or between an intense sweetener and a bulk sweetening agent, or alternatively between two different bulk sweetening agents. Patents U.S. Pat. No. 4,986,991 and EP 366,251 may be mentioned by way of example, these relating respectively to a synergistic composition between sucralose and aspartame and to a synergistic composition based on sucralose and maltitol, which are useful in the formulation of chewing-gums. There may also be mentioned Patent EP 453,402, which claims the use of a synergistic mixture comprising sugar and xylitol in order to obtain better-tasting chewing-gums, or alternatively Patent U.S. Pat. No. 5,017,400 relating to a synergistic composition based on xylitol and maltitol which may be used, for example, in the preparation of chewing-gums having a more intense sweet taste.

The methods constituting this third group and claiming the use of specific substances, in low concentrations, in order to emphasize the perception of the chewing-gum flavourings, are not without flaws. They occasionally give rise to strange or artificial tastes, or destroy the harmony constituted by a flavouring per se, masking certain notes and rendering certain others cruder and more exacerbated. The original balance of the flavouring can then only be regained by correction of the amounts of the various constituents of the flavouring, these constituents generally being very high in number, especially in the case of natural flavourings. The difficulty of achieving such a correction is clear.

A fourth group of methods which enables the taste of a chewing-gum and, at the very least, its sweetness profile, to be modified consists in adjusting the particle size of the water-soluble sweetening agents provided in pulverulent form and used in the formulation of a chewing-gum.

Patent EP 427,541 is known in particular, which claims the use of sucrose containing more than 60% of particles with a diameter less than 325 mesh (45 microns) for the purpose of increasing the sweet sensation in chewing-gums. It is simultaneously recommended, in order to enhance the aromatization, to increase the content of gum base by at least 25% relative to the usual formulations and to do likewise as regards the flavouring content. This unfortunately, as indicated above, has detrimental consequences on the cost price, but also on the ability of the chewing-gum to be chewed easily.

Patent U.S. Pat. No. 4,900,563 is also known, this relating to an anhydrous chewing-gum comprising pulverulent fructose with a particle size of less than 70 mesh (212 microns). Unfortunately, as for sucrose, fructose is cariogenic and consequently does not enable, as is often desired, noncariogenic chewing-gums to be prepared.

Patent U.S. Pat. No. 4,803,083 is also known, this relating to the use of two sorbitol powders of different particle sizes to prepare sugar-free chewing-gums. In this case, the patent concerns above all the improvement of the manufacturing conditions and of the texture of the manufactured products. Although more concern is shown for the difference existing between the particle sizes of two powders than for the particle sizes themselves, it should be pointed out that, apparently, one of them has an average diameter in the region of 75 microns and the other has a preferred average diameter which is considerably larger than this value, fairly close to 200 microns according to the description. Thus, non-cariogenic chewing-gums may be prepared, but, as will be seen below, the particle size recommended here for sorbitol is not that which should be chosen for a pulverulent maltitol of high purity.

The Applicant Company has observed, surprisingly and unexpectedly, that the organoleptic quality of a chewing-gum, and in particular the taste and the aromatization in terms of impact and duration, could be improved by incorporating therein, as pulverulent phase, maltitol having a maltitol purity greater than 95% and a particle size such that 50% of the maltitol particles within the chewing-gum are smaller than 90 microns in size.

Under these conditions, excellent recovery of the flavouring is observed, without deformation of the aromatic notes of the latter. It is thus not absolutely necessary to adjust the composition of the flavouring as the latter is already suitable for formulating a standard chewing-gum, that is to say a chewing-gum mainly containing sucrose.

In the present invention, the term "aromatic note" refers to the retro-olfactory sensation which may be attributed specifically to a flavouring compound considered in isolation or in relation with other molecules constituting the flavouring.

In the present invention, the term "improvement of the organoleptic quality" will be understood to mean the improvement of all the sensory factors, namely the taste, the aromatization and the texture.

The Applicant Company has, indeed, verified that when the purity of the powder, this value being readily determined by chromatography, is of the order of 83% to 94%, chewing-gums which were excessively hard and difficult to chew were then obtained, for an identical formulation. In order to correct the texture, it then proves to be essential to increase the content of gum base and to increase the flavouring content in parallel. Another solution consists in choosing a more supple gum base. However, this leads in all cases to a rise in the cost of the formulation, without any organoleptic benefit, in contrast with what might have been expected by complying, in particular, with the indications of Patent EP 427,541 mentioned above. Furthermore, when the maltitol is low in purity, the Applicant Company has observed that, no doubt on account of their crystallinity which is then necessarily low, the maltitol particles dissolve too rapidly and the sweet taste does not then accompany the flavouring correctly.

Without wishing to make reference to any particular theory, when it is desired to obtain an improved aromatization in terms of impact and of duration, it would appear, as the Applicant has just observed, that there is an ideal particle size corresponding to each chewing-gum sweetener and to each level of purity for a chosen sweetener, fructose apparently needing to be coarser than sucrose, maltitol needing to be finer, for example, than sorbitol, and high-purity maltitol needing to be finer than low-purity maltitol. In the case of a maltitol with a purity greater than 95%, the ideal particle size within a chewing-gum is that which is specified above.

A great many documents teach of the possibility of using maltitol in the formulation of a chewing-gum, but none of them envisages incorporating, as a pulverulent phase for the latter, a maltitol powder of high purity and of suitable particle size.

The Patent applications and Patents WO 88/08671, U.S. Pat. No. 4,217,368, EP 302,023, EP 425,115, U.S. Pat. No. 5,110,608 and U.S. Pat. No. 5,075,118, for example, teach of the possibility of selecting, from among several polyols or several sweeteners, maltitol in order to formulate a chewing-gum. The physical state of this maltitol is not specified, or is not considered to be of vital importance. Such a physical state may thus either be a syrup or a powder.

Examples of the use of a hydrogenated maltose syrup or powder in order to protect and to encapsulate aspartame intended, in particular, for the preparation of noncariogenic chewing-gums are given in Patent application WO 85/01862. The physical state of the hydrogenated maltose and its purity appear to be irrelevant. The particle size of the aspartame powder encapsulated in the hydrogenated maltose is, on the other hand, between 40 and 140 mesh, that is to say between 106 and 425 microns, which is far from being the ideal particle size for a high-purity maltitol powder, as the Applicant has observed.

Patents JP 74,32067 and JP 77,27702 and Patent application JP 03,133,341 are examples of processes for the preparation of chewing-gums containing maltitol combined with sugar, lactose, dextrose, glucose syrups, mannitol, sorbitol or honey. The physical state and the purity of the maltitol used are never specified.

The document "Chewing-gum sans sucre à base de maltitol" [Sugar-free chewing-gum based on maltitol] by T. Maruyama et al., published in Shokuhin Kogyo (1984), 27, No. 24, p. 73–80 and Patent EP 325,090 both teach of the possibility of using maltitol as a replacement for sorbitol in order to prepare non-cariogenic chewing-gums of very low hygroscopicity. Although the physical state of the maltitol is not clearly specified, it is possible to think that it should be used in pulverulent form. However, it is in no way indicated to select a preferable particle size or a preferable particular purity for the maltitol.

Other documents teach more specifically of the possibility of using a maltitol powder whose purity is specified.

The document "Evaluation of maltitol in eight food products: comparison with sucrose, fructose and sorbitol" by R. L. De Fielliettaz Goethart et al. published in Basic Studies in Food Science (1983), vol. 2, p. 8–9, is based on works relating to the use, in the formulation of chewing-gums, of a crystalline powder containing 88% of maltitol. It appears that maltitol has a sweetening power which is greater than that of sorbitol and less than that of sugar. The technological properties of maltitol are estimated to be entirely comparable with those of sorbitol. In "Malbit® and its application in the food industry" in "Developments in Sweeteners", vol. 3 (1987), p. 83–108, Y. Fabry also discloses a chewing-gum formulation containing the same maltitol powder MALBIT®, which has, as we are reminded, a maximum maltitol purity of 90% and a particle size in the region of 20 mesh (850 microns) or of 50 mesh (300 microns).

Finally, three other documents are known describing chewing-gums containing maltitol in a purity which may be upto 99%.

Patent FR 2,499,576 thus relates, in Example 12, to a chewing-gum comprising 30 parts of anhydrous maltitol crystals of purity in the region of 99.2%. The particle size of this maltitol powder is not specified.

As regards Patent EP 185,595, this describes in Example 6 a chewing-gum comprising a maltitol crystallized from water, with a purity of 94.8% and 65% of the particles of which are larger than 160 microns in size.

The third document is Patent U.S. Pat. No. 5,017,400 which, as pointed out above, concerns a synergistic composition based on xylitol and maltitol. This composition may, as indicated in Example 1, be a ground crystallized powder with a purity of 99%. The particle size of this powder is not specified.

In summary, none of the above documents teaches of, or even gives a suggestion of, the advantage of incorporating, as pulverulent phase for a chewing-gum, a maltitol powder of high purity and of suitable particle size in order to obtain the desired result in the present invention.

The subject of the invention is thus a novel chewing-gum composition essentially composed of a gum base, a flavouring and pulverulent maltitol, characterized in that the said maltitol has a maltitol purity greater than 95% and a particle size distribution such that at least 50% in number of the maltitol particles present within the composition are smaller than 90 microns in size.

The composition is thus of improved organoleptic quality, that is to say of better taste and of better aromatization in terms of impact and duration, but also has an excellent texture, is soft and is stable on chewing and over time. The subject of the invention is thus also a chewing-gum composition which is improved from the point of view of its organoleptic quality, comprising:

a gum base, a sweetening filler comprising pulverulent maltitol, which has a maltitol purity greater than 95% and a particle size distribution such that at least 50% in number of the maltitol particles present within the composition are smaller than 90 microns in size, optionally other sweetening agents, optionally a binding agent, a flavouring agent.

The particle size distribution of the pulverulent maltitol has, as indicated above, a great influence on the desired effect. Within the chewing-gum composition, it is preferably such that at least 50% in number of the maltitol particles are smaller than 75 microns in size. When the pulverulent maltitol is even more finely divided within the chewing-gum, that is to say when more than half of the particles are smaller than 60 microns in size, the desired effect is even greater. The Applicant Company has observed that the ideal is to obtain at least 50% of particles smaller than 40 microns in size within the chewing-gum.

This particle size distribution of the pulverulent maltitol within the chewing-gum is readily measured by interference contrast photon microscopy on a slice of chewing-gum 20 microns in thickness which has been prefrozen at −20° C.

The particle size of the pulverulent maltitol given above is that, as observed by the Applicant, which should be selected for a maltitol powder of very high purity. The desired effect is then maximal and the texture remains chewable with ordinary gum bases. There is then no obligation, contrary to that which should be done for a maltitol powder of low purity and contrary to the teaching, in particular of Patent EP 427,541, to increase the amounts of gumbase and, in parallel, the amounts of flavouring. The choice of a pulverulent maltitol of high purity is also justified, as observed by the Applicant Company, for technological reasons associated with the greater ease of grinding, the reduced production of dusts and the greater ease of storage with a reduced risk of lumping together, when compared with a maltitol powder with a purity of less than 95%.

It is hence preferred to incorporate into the chewing-gum composition in accordance with the invention pulverulent maltitol with a purity greater than 98%, preferably greater than 99% and more preferably greater than 99.5%.

Measurement of the purity of the pulverulent maltitol distributed within the chewing-gum may be performed by gas chromatography after silylation. Quantification is then achieved by the internal calibration method, using a maltitol powder of known purity.

The maltitol particles are highly crystalline. Their heat of fusion exceeds 125 joules per gram and ordinarily exceeds 140 joules per gram, or even 160 joules per gram. Furthermore, these particles preferably have a melting point, measured by differential calorimetric analysis, above 145° C. and more preferably above 147° C.

It should be noted that the purer the pulverulent maltitol, the more frequent was the observation that it was advantageous to incorporate very fine particles into the chewing-gum composition. It would thus seem that there is a direct relationship between purity and particle size in order to obtain an improved taste and a chewable texture which remain stable.

The pulverulent maltitol possessing within the chewing-gum composition the properties stated above may represent approximately 2% to approximately 85% of the composition. The effect is proportionally greater the higher the concentration thereof. For this, it is preferred to select amounts between 5% and 75%, and preferably strictly between 10% and 75%, of the composition.

The gum base constituting the chewing-gum composition is preferably an ordinary gum base similar to those which are commonly used. Depending on whether it is a chewing pastille, a bubble-gum, a sugar-coated center or a low-calorie chewing-gum, the gum base may represent approximately 15% to approximately 70% of the composition in accordance with the invention. Its nature will also be adapted to the type of chewing-gum manufactured. It may comprise synthetic and/or natural elastomers such as polyisoprene, polyvinyl acetate, polyisobutylene, latexes, resins such as terpene resins, polyvinyl esters and alcohols, fats or waxes such as, for example, lanolin, vegetable oils which may or may not be partially hydrogenated, fatty acids, partial esters of glycerol, paraffin, microcrystalline waxes, filling agents such as talc, calcium carbonate, elastomeric plasticizers such as glyceryl triacetate, glyceryl monostearate, rosin derivatives, emulsifiers such as lecithin, sorbitol esters, dyes or bleaching agents, antioxidants, and anti-sticking agents such as mannitol.

The content of gum base in the composition in accordance with the invention is preferably between 15% and 40%. In most cases, this content is between 18% and 28%, that is to say slightly below the usual contents of the sugar-free chewing-gums on the market formulated with sorbitol as predominant pulverulent bulk sweetener.

The chewing-gum composition in accordance with the invention also contains a flavouring agent. This agent may comprise natural and/or synthetic compounds. These may, in particular, be mint, cinnamon, orange, lemon or lime flavourings or flavourings corresponding to other fruit or plants such as, for example, apple, strawberry, banana, cherry or mixed-fruit flavourings.

The flavouring agent is used in an appropriate amount which may readily be determined by a person skilled in the art using simple routine tests, by considering the nature of the gum base, the amount of gum base, the type of chewing-gum and the properties of this flavouring agent. Ordinarily, it will be used in a proportion between approximately 0.2% and approximately 3%. Preferably, and in particular for hydrophobic flavouring agents, sufficient amounts will be selected in order to plasticize the gum base without this becoming excessively soft. For this, a flavouring agent content between 0.5% and 1.8% will be chosen instead, the ideal being to choose a content between 0.8% and 1.5%.

The dose of flavouring agent will also depend on the richness of the latter in flavouring compounds, that is to say in compounds having a genuine retro-olfactory effect. Furthermore, this dose will vary with the physical nature of the flavouring agent. For example, for an encapsulated form, the dose will ordinarily be lower.

The flavouring agent may be provided in the form of a single product or in two or more different physical forms essentially comprising the same flavouring compounds.

Several flavouring agents of various natures and of identical or different physical states may also be used.

The chewing-gum composition according to the invention may comprise a binding agent, in a concentration of 0.1% to 30%. This binding agent may preferably be chosen from water, glycerol, hydrogenated or unhydrogenated mono-, di-, oligo- or polysaccharide syrups, and syrups of low-calorie fillers and any mixtures thereof.

The water in the chewing-gum may be provided in the form of free water or by other constituents.

The mono-, di-, oligo- or polysaccharide syrups may, for example, be syrups of xylitol, of sorbitol, of maltitol, of lactitol, of isomaltulose, of hydrogenated isomaltulose, of erythrose, of erythritol, syrups, which are preferably hydrogenated, derived from the hydrolysis of starches or of inulins, containing oligosaccharides and/or polysaccharides. As regards the syrups of low-calorie fillers, it is particularly preferred to choose syrups of polydextrose, of polyglucose or of dextrin.

The composition according to the invention may also contain additional sweetening agents in dry or liquid form. These may be bulk sweeteners and/or intense sweeteners having a sweetening power at least ten times greater than that of sucrose. Among the bulk sweeteners, it may in particular prove advantageous to use mannitol in order to prolong the sweet taste, to use erythritol and xylitol in order to provide a certain freshness, or to use pulverulent sorbitol or a maltitol powder with a purity below 95% in order to adjust the texture and make the latter firmer. When a maltitol powder with a purity between 82 and 94% is added, for example with this aim, it may optionally be added as a premix in any proportion with pulverulent maltitol of purity greater than 95%, or alternatively with another ingredient of the composition according to the invention. This composition may also comprise intense sweeteners such as aspartame, alltame, acesulfame and sucralose, in free and/or encapsulated form.

Food acids may also be added to the composition in accordance with the invention, for example as exhausters, in low contents, especially when a fruit flavouring is used.

The subject of the present invention is also a process which enables the taste and texture of a chewing-gum to be improved, but which also enables the improved recovery of the flavouring present in a chewing-gum. This process applies in particular to a sugar-free chewing-gum. The process consists in choosing and in using a particular pulverulent maltitol, such that the chewing-gum after manufacture contains maltitol particles with a maltitol purity greater than 95% and a particle size distribution such that at least 50% of them are smaller than 90 microns in size, preferably smaller than 75 microns and more preferably smaller than 60 microns, within the chewing-gum. The ideal is to make it such that more than half of the maltitol particles in the chewing-gum are smaller than 40 microns. The principal process consists in choosing an appropriate maltitol composition. After many tests, the Applicant has observed, surprisingly and unexpectedly, that it was suitable to select and use a composition whose particle size, compressibility and maltitol purity were adjusted according to the type of chewing-gum to be formulated. This maltitol composition is not necessarily totally anhydrous in all cases.

The application Company has observed, surprisingly, that there was a direct relationship between the ability of a powder to give hard tablets, that is to say to be compressible, and the particle size to be selected in order to obtain an improved taste and a chewable texture which remains stable during chewing and on ageing.

Firstly, when it is desired to prepare a chewing-gum which has to be of improved organoleptic quality and has, furthermore, to be virtually devoid of liquid phase, that is to say of water and of glycerol, it may be chosen to employ a poorly compressible pulverulent maltitol, which may then have a particle size in the region of or very slightly coarser than that which should be obtained within the chewing-gum. A highly compressible pulverulent maltitol may also be selected. In this case, it is preferable to select a considerably larger particle size than that which it is desired to obtain at the end in the chewing-gum.

A compressibility is considered to be low in the present invention when a value below 80 N according to the "test A" method described in Patent EP 220,103, of which the Applicant is the proprietor, is obtained for the pulverulent maltitol selected. A compressibility is considered as being high in the contrary case, that is to say when this value exceeds 80 N.

Test A consists in measuring the force, expressed in newtons, which is representative of the compressibility of the pulverulent maltitol studied and which is necessary to crush a tablet prepared from the said maltitol, that is to say to cause the appearance of rupture lines within the bulk constituting the latter, this force thus reflecting the crush strength of the tablet, which is cylindrical with plane faces having a diameter of 13 nun, a thickness of 5 nun and a weight of 0.896 g, that is to say having an apparent voluminal mass of 1.35 g/ml, the said force being exerted against the peripheral surface of the tablet in the direction of the axis of revolution of the latter, using a movable stop applied against the said surface along a generatrix, the said tablet furthermore being immobilized against a fixed stop also applied against the peripheral surface of the tablet along a generatrix diametrically opposite to that against which the movable stop is applied.

Thus, when the pulverulent maltitol is composed of crystals obtained by crystallization from water, with a purity exceeding 95% and having a compressibility below 8 N in test A and usually in the region of 45 N, it is possible to choose a particle size substantially identical to that which it is desired to obtain in the chewing-gum devoid of liquid phase, that is to say such that at least 50% of the particles are smaller than 90 microns in size.

On the other hand, for a product of high purity and high compressibility, such as that forming the subject of the invention of Patent EP 220,103, the Applicant has observed that it was possible to choose, without this being obligatory but merely preferred, a coarser particle size, that is to say one such that at least 50% of the particles are smaller than 120 microns, or even 150 microns, in size. In this manner, it is thus possible to obtain within the chewing-gum, after manufacture, the ideal particle size distribution as regards the taste and the texture.

In order to achieve this result, it is also possible to select a mixture of a poorly compressible high-purity pulverulent maltitol and a highly compressible maltitol powder having a purity of less than 95% of maltitol.

Secondly, when it is desired to prepare a chewing-gum containing only glycerol as the liquid phase, that is to say one virtually devoid of water, the principle outlined above may be adopted except when the process for the manufacture of the chewing-gum with glycerol imposes, during the mixing or the extrusion, severe temperature conditions in the presence of the maltitol composition. It is, indeed, possible in this case to choose, as the Applicant has observed, a particle size which is slightly coarser still than that which is suitably selected for a chewing-gum virtually devoid of liquid phase.

This may be explained by the fact that high-purity crystalline maltitol is slightly soluble in anhydrous glycerol. Indeed, its solubility at 68° C., at 90° C. and at 115° C. is respectively close to 5%, to 20% and to 50% in the medium in question, which is by no means negligible. Consequently, at high temperature, the maltitol appears to be capable of dissolving in the glycerol within the chewing-gum. Thus, a fairly coarse particle size may be chosen in order to formulate an anhydrous chewing-gum with glycerol when working at a high mixing or extrusion temperature.

Thirdly, when it is desired to formulate a chewing-gum containing water, in an amount of 0.1% to 6%, it is possible to choose a maltitol composition which is proportionally coatset the more compressible it is, the higher the mixing or extrusion temperatures and the higher the water and glycerol contents contained within the chewing-gum. By taking the simple rules stated above into consideration, it will fall to a person skilled in the art to choose the appropriate particle size of the high-purity pulverulent maltitol in order to obtain a distribution within the chewing-gum such that at least 50% of the maltitol particles are smaller than 90 microns in size.

It should, moreover, be noted that thought must be given, in order to determine the appropriate particle size, to the moment chosen during the process at which to introduce the pulverulent maltitol. Indeed, by selecting an excessively fine powder and by introducing it at the very start of manufacture, the maltitol is generally overly soluble, especially when working at raised temperature and in the presence of large amounts of water or of glycerol. Consequently, the chewing-gum paste has a tendency in this case to become sticky, which does not fail to pose problems during manufacture. Moreover, on cooling and on storage, the dissolved maltitol is then led to crystallize out and the chewing-gum may contain coarse particles and no longer have a correct aromatization in terms of impact and duration.

Consequently, excessive dissolution of the pulverulent maltitol should be avoided as far as possible by means of the judicious choice of a correct particle size as a function of the manufacturing parameters and of the formulation selected.

These three types of chewing-gum may be manufactured without drawbacks by using the processes and methods known per se for chewing-gums. The final products may be sold equally well as chewing pastilles and as sugar-coated sticks or balls of gum or alternatively as bubble-gums intended in particular for children.

Finally, the subject of the invention is, as a novel product, a pulverulent maltitol which is intended in particular for the preparation of a chewing-gum of improved organoleptic quality. The pulverulent maltitol in accordance with the invention is special in the sense that it is both of extremely high purity and of well-chosen fine particle size. Its maltitol purity, which may be quantified by high performance liquid chromatography on an ion-exchange resin in calcium form, should be greater than 95%.

The particle size of the pulverulent maltitol, which may be determined by observation under a microscope, should be such that at least 50% in number of the particles are smaller in size, expressed in microns, than 1.5 times the compressibility value of the said maltitol expressed in newtons (N) and determined in test a as described in the abovementioned Patent EP 220,103. Furthermore, the pulverulent maltitol in accordance with the invention preferably has a content of less than 35%, relative to the weight of the pulverulent maltitol, of particles smaller than 10 microns in size.

The purity, which reveals itself to be a parameter of great importance in relation to the ease of grinding, the texture and the perception of the flavourings in a chewing-gum, is preferably greater than 98%, more preferably greater than 99% and better still greater than 99.5%.

Ordinarily, the particles of the pulverulent maltitol have a heat of fusion greater than 140 joules per gram, or even 160 joules per gram, and a melting point above 145° C. and preferably above 147° C.

As regards the particle size, the pulverulent maltitol preferably comprises highly crystalline particles of particle size such that 50% in number of these particles are smaller in size, in microns, than 1.2 times, and more preferably than 0.8 times, the compressibility value obtained in newtons in the abovementioned test A.

Finally, the content of particles smaller than microns in size, which are revealed to be those which create the most dust in production sites and are those capable of dissolving most rapidly in the liquid phase of a chewing-gum, is preferably less than 25%, more preferably less than 15% and better still less than 5%, of the weight of the pulverulent maltitol.

The invention will be better understood by means of the examples which follow.

EXAMPLE 1: Effect of the particle size

Flavoured chewing-gum compositions are prepared according to the base formulation below:

DREYCO® gum base (Dreyfus): 20%

Maltitol powder: 63.7

Concentrated LYCASIN® 80/55, marketed by the Applicant Company: 15

Glycerol: 0.5

Natural mint flavouring (Silesia): 0.8

The gum base is introduced into a kneading blender equipped with two Z-arms and a jacket, maintained at a temperature of 50° C. by circulation of water within the jacket. After blending the gum base for about 5 minutes, about one-third of the maltitol powder is added and mixed intimately with the gum base. The mixture is blended continuously for 2 minutes, followed by addition of a second third of the maltitol powder and the amount of LYCASIN® 80/55 preheated to 55° C. After about 2 minutes of additional blending, the remaining amount of maltitol powder and the glycerol are introduced. Finally, after blending for 2 minutes, the liquid mint flavouring is added. Blending is continued for a further 1 minute so as to obtain a homogeneous paste. This paste is then removed from the kneading machine, laminated and cut into sticks millimeters in thickness.

According to this formulation, five chewing-gum compositions are prepared using the five maltitol powders below, all of purity greater than 95% and all obtained by crystallization from water. These powders have a compressibility in the region of 45 N in test A, and have the following properties:

| Powder A: | |
|---|---|
| Maltitol purity (by liquid phase chromatography) | 99.6% |
| Water content (Karl Fisher method) | 0.27% |
| Melting point | 148° C. |
| Powder B: | |
| Maltitol purity | 99.1% |
| Water content | 0.44% |
| Melting point | 149° C. |
| Powder C: | |
| Maltitol purity | 98.4% |
| Water content | 0.29% |
| Melting point | 147° C. |
| Powder D: | |
| Maltitol purity | 99.4% |
| Water content | 0.26% |
| Melting point | 148.5° C. |
| Powder E: | |
| Maltitol purity | 98.4% |
| Water content | 0.32% |
| Melting point | 147° C. |

The particle size distributions of these powders are such that 50% by weight of the maltitol particles have a size in the region of:

−150 microns for powder A
95 microns for powder B
75 microns for powder C
60 microns for powder D
40 microns for powder E 1.1) Hardness measurements Comparison is made between the hardnesses, for the five chewing-gum compositions, of sticks 0.5 centimeter in thickness, 8 days old and stored in the absence of moisture at 20° C., by penetrometry using an INSTRON® brand machine.

The average hardness results (average values for 10 sticks) are as follows:

Powder A: 32.0 N

Powder B: 35.3 N

Powder C: 25.6 N

Powder D: 35.9 N

Powder E: 35.4 N

It is observed that the chewing-gum compositions have fairly similar hardnesses, except in the case of the use of powder C, in which the sticks obtained are more supple.

For all of the compositions, the textures are considered to be good, or even very good.

1.2) Taste assessment

In a blind test, a panel of 25 people is asked to grade the five chewing-gum compositions from 0 to 4 in order of preference (grade 0 for the product considered to have the poorest taste and grade 4 for the preferred product).

These grades are then combined and interpreted, taking the comments of each taster into account.

The composition comprising powder A is that which obtains the lowest score (1.2).

This composition differs significantly from the other compositions tested as regards the average grade awarded. Furthermore, during the first seconds of chewing, the perception of the flavour is considered to be too delayed for this composition. The sweet taste is intense but transient and does not correctly accompany the perception of the flavour. This is not the case for the compositions based on powders B, C, D and E, the taste and aromatization of which are greatly improved in terms of impact and duration.

The preferred compositions are those which comprise powders C, D and E. They obtain scores of between 2.9 and 3.8, which is noteworthy.

1.3) Size of the particles within the chewing-gum compositions.

The particle size distributions of the pulverulent maltitol within the compositions are assessed by differential contrast photon microscopy on chewing-gum slices which have been pre-frozen at −20° C. These slices are approximately 20 microns in thickness. It is observed that these particle size distributions are in all cases approximately 10% lower than those of the maltitol powders used. These distributions are such that at least 50% of the maltitol particles are smaller than 90 microns in size and are thus in accordance with the invention, except in the case of the use of powder A, in which the particles are coarser.

EXAMPLE 2: Effect of the maltitol purity

Six other chewing-gum compositions are prepared using the formulation and the procedure given in Example 1, but incorporating the following maltitol powders into these compositions:

Powder C

Powder E

A powder F having:

A compressibility in test A in the region of 55 N

A maltitol purity of 83.9%

A water content of 1.9%

A sorbitol content of 4.4%

A melting point of 120° C.

A particle size distribution such that, in numerical terms, 50% of the maltitol particles are in the region of 75 microns in size.

A powder G having:

A compressibility in test A in the region of 175 N

A maltitol purity of 92.6%

A water content of 1.1%

A sorbitol content of 1.7%

A melting point of 135° C.

A particle size distribution such that, in numerical terms, 50% of the maltitol particles are in the region of 90 microns in size A powder H having:

A compressibility in test A in the region of 180 N

A maltitol purity of 94.0%

A water content of 1.0%

A sorbitol content of 1.2%

A melting point of 143° C.

A particle size distribution such that, in numerical terms, 50% of the maltitol particles are in the region of 20 microns in size.

A powder I having:

A compressibility in test A in the region of 50 N

A maltitol purity of 99.4%

A water content of 0.5%

A sorbitol content of 0.3%

A melting point of 147.6° C.

A particle size distribution such that, in numerical terms, 50% of the maltitol particles are in the region of 65 microns in size.

For convenience, Composition C, Composition E, Composition F, Composition G, Composition H and Composition I will be referred to respectively as the chewing-gum compositions obtained.

Compositions G and H exhibit poor binding and poor homogeneity.

In contrast, the other chewing-gum compositions appear to be acceptable after manufacture.

2.1) Hardness measurements

The following results were obtained on sticks 0.5 centimeter in thickness stored at 20° C. in the absence of moisture for 1 day and 8 days after manufacture.

| Composition C | |
|---|---|
| at 1 day: | 20.0 N |
| at 8 days: | 25.8 N |
| Composition E | |
| at 1 day: | 24.5 N |
| at 8 days: | 35.4 N |
| Composition F | |
| at 1 day: | 27.7 N |
| at 8 days: | 60.9 N |
| Composition G | |
| at 1 day: | 74.2 N |
| at 8 days: | 91.1 N |
| Composition H | |
| at 1 day: | 100.0 N |
| at 8 days: | 91.1 N |
| Composition I | |
| at 1 day: | 31.4 N |
| at 8 days: | 44.4 N |

One day after manufacture, Compositions G and H are excessively hard. The textures of these products also appear to be incorrect 8 days after manufacture, both on chewing and by penetrometry.

These textures may be improved either by increasing the gum base content or by choosing a gum base of considerably higher plasticity.

Compositions F and I are relatively hard after one day.

These textures are considered to be acceptable. On the other hand, after 8 days, Composition F becomes very difficult to chew, this not being the case for Composition I, which appears to be stable over time.

Compositions C and E are also stable and retain a correct texture and are easy to chew.

In summary, only the use of maltitol powders of purity greater than 95% and of correct particle size is suitable for the production of stable chewing-gum compositions which remain chewable.

2.2)Taste assessment

It would appear that the hardness results obtained by the panel of tasters in Example 1 are in total agreement with those obtained by instrumental means and given above.

In terms of taste, Compositions C, E and I are significantly preferred when compared with the other compositions, on account of the appearance of the flavour within the first ten seconds of placing in the mouth and on account of the long persistence of the sweet taste and of the flavouring during chewing.

We claim:

1. Chewing-gum composition containing a gum base, a flavouring agent and a sweetening filler comprising pulverulent maltitol, wherein said pulverulent maltitol has a maltitol purity greater than 95% and a particle size distribution such that at least 50% of the maltitol particles present within the composition are smaller than 90 microns in size.

2. Chewing-gum composition according to claim 1, wherein the maltitol has a particle size distribution such that at least 50% of the particles are smaller than 75 microns in size.

3. Chewing-gum composition according to claim 2, wherein the maltitol has a particle size distribution such that at least 50% of the particles are smaller than 60 microns in size.

4. Chewing-gum composition according to claim 3, wherein the maltitol has a particle size distribution such that at least 50% of the particles are smaller than 40 microns in size.

5. Chewing-gum composition according to claim 1, wherein the maltitol has a maltitol purity greater than 98%.

6. Chewing-gum composition according to claim 5, wherein the maltitol has a maltitol purity greater than 99%.

7. Chewing-gum composition according to claim 6, wherein the maltitol has a maltitol purity greater than 99.5%.

8. Chewing-gum composition according to claim 1, wherein the maltitol represents from approximately 2 to approximately 85% of the composition.

9. Chewing-gum composition according to claim 8, wherein the maltitol represents from 5% to 75% of the composition.

10. Chewing-gum composition according to claim 9, wherein the maltitol represents from 10% to 75% of the composition.

11. Chewing-gum composition according to claim 1, in which the flavouring agent represents approximately 0.2% to approximately 3% of the composition.

12. Chewing-gum composition according to claim 11, in which the flavouring agent represents from 0.5% to 1.8% of the composition.

13. Chewing-gum composition according to claim 12, in which the flavouring agent represents from 0.8% to 1.5% of the composition.

14. Chewing-gum composition according to claim 1, additionally comprising a binding agent or other sweetening agents than the sweeteing filler comprising pulverulent maltitol.

15. Chewing-gum composition according to claim 1, additionally comprising a maltitol powder having a purity of less than 95%.

16. Process for the manufacture of a chewing-gum having improved taste and texture comprising the steps of
   a) selecting a sweetening filler comprising pulverulent maltitol having a maltitol purity greater than 95% and having a particle size distribution and a compressibility chosen such that at least 50% of the maltitol particles present within the chewing-gum after its manufacture, are smaller than 90 microns in size,
   b) blending said sweetening filler with a gum base and a flavouring agent, to obtain said chewing-gum.

17. Process for the manufacture of a chewing-gum having improved taste and texture comprising the steps of
   a) selecting a sweetening filler comprising pulverulent maltitol having a maltitol purity greater than 95% and a particle size such that at least 50% in number of the particles are smaller in size, expressed in microns, than 1.5 times the compressibility value of the said maltitol, determined in a test A consisting in measuring the force, expressed in newtons, necessary to crush a tablet prepared from the said maltitol, that is to say to cause the appearance of rupture lines within the bulk constituting the latter, this force thus reflecting the crush strength of the tablet, which is cylindrical with plane faces having a diameter of 13 mm, a thickness of 5 mm and a weight of 0.896 g, that is to say having an apparent voluminal mass of 1.35 g/ml, the said force being exerted against the peripheral surface of the tablet in the direction of the axis of revolution of the latter, using a movable stop applied against the said surface along a generatrix, the said tablet furthermore being immobilized against a fixed stop also applied against the-peripheral surface of the tablet along a generatrix diametrically opposite to that against which the movable stop is applied,
   b) blending said sweetening filler with a gum base and a flavouring agent, to obtain said chewing-gum.

18. Sweetening filler comprising pulverulent maltitol having a maltitol purity greater than 95% and a particle size such that at least 50% in number of the particles are smaller in size, expressed in microns, than 1.5 times the compressibility value of the said maltitol, determined in a test A consisting in measuring the force, expressed an newtons, necessary to crush a tablet prepared from the said maltitol, that is to say to cause the appearance of rupture lines within the bulk constituting the latter, this force thus reflecting the rush strength of the tablet, which is cylindrical with plane faces having a diameter of 13 mm, a thickness of 5 mm and a weight of 0.896 g, that is to say having an apparent voluminal mass of 1.38 g/ml, the said force being exerted against the peripheral surface of the tablet in the direction of the axis of revolution of the latter, using a movable stop applied against the said surface along a generatrix, the said tablet furthermore being immobilized against a fixed stop also applied against the peripheral surface of the tablet along a generatrix diametrically opposite to that against which the movable stop is applied.

* * * * *

UNITED STATES PATENT AND TRADEMARK OFFICE
CERTIFICATE OF CORRECTION

PATENT NO. : 5,547,689
DATED : August 20, 1996
INVENTOR(S) : Ribadeau-Dumas, et. al.

It is certified that error appears in the above-indentified patent and that said Letters Patent is hereby corrected as shown below:

Column 8, line 63, delete "alltame" and insert --alitame--.
Column 9, line 52, delete "13 nun" and insert --13mm--; and delete "5nun" and insert --5mm--.
Column 10, line 42, delete "coatset" and insert --coarser--.
Column 11, line 21, delet "in test a" and insert --in test A--;
    line 41, delete "than microns" and insert --than 10 microns--;
    line 56, after "63.7" insert --%--;
    line 58, after "15" insert --%--;
    line 60, after "0.5" insert --%--;
    line 61, after "0.8" insert --%--.
Column 12, line 9, delete "sticks millimeters" and insert --sticks 5 millimeters--;

Claim 17, column 16, line 40, delete "the-peripheral" and insert --the peripheral--.

Claim 18, column 16, line 50, delete "expressed an newtons" and insert --expressed in newtons--;
    line 54, delete "rush strength" and insert --crush strength--;
    line 57, delete "1.38g/ml" and insert --1.35g/ml--.

Signed and Sealed this

Eleventh Day of February, 1997

Attest:

BRUCE LEHMAN

Attesting Officer      Commissioner of Patents and Trademarks